US009399108B2

United States Patent
Bird

(10) Patent No.: US 9,399,108 B2
(45) Date of Patent: *Jul. 26, 2016

(54) PORTABLE SEDATION APPARATUS AND RELATED METHOD

(71) Applicant: Erin Bird, Salado, TX (US)

(72) Inventor: Erin Bird, Salado, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/531,722

(22) Filed: Nov. 3, 2014

(65) Prior Publication Data

US 2015/0053208 A1   Feb. 26, 2015

Related U.S. Application Data

(63) Continuation of application No. 13/548,894, filed on Jul. 13, 2012, now Pat. No. 8,881,722, which is a continuation of application No. 12/569,618, filed on Sep. 29, 2009, now Pat. No. 8,251,058.

(51) Int. Cl.
| | |
|---|---|
| *A61M 11/00* | (2006.01) |
| *A61M 16/10* | (2006.01) |
| *A61M 16/00* | (2006.01) |
| *A61M 16/06* | (2006.01) |
| *A61M 16/20* | (2006.01) |

(Continued)

(52) U.S. Cl.
CPC ......... *A61M 16/104* (2013.01); *A61M 16/0003* (2014.02); *A61M 16/009* (2013.01); *A61M 16/0057* (2013.01); *A61M 16/06* (2013.01); *A61M 16/1005* (2014.02);

(Continued)

(58) Field of Classification Search
CPC ............... A61M 16/06; A61M 2202/0283; A61M 2230/437; A61M 2202/0208; A61M 2016/0042; A61M 2016/1035; A61M 16/009; A61M 16/22; A61M 2016/0039; A61M 16/104; A61M 16/0003; A61M 16/1005; A61M 16/205; A61M 16/0057; A61M 16/12; A61M 2016/0036; A61M 2202/0241; A61M 2205/3334; Y02C 20/10
USPC ............ 128/203.12, 200.22, 203.23, 203.22, 128/204.12, 206.11, 207.13, 207.18, 206.18
See application file for complete search history.

(56) References Cited

U.S. PATENT DOCUMENTS

| 3,985,332 A | 10/1976 | Walker |
|---|---|---|
| 4,259,303 A | 3/1981 | Nakaji |

(Continued)

FOREIGN PATENT DOCUMENTS

| EP | 1416218 | 6/2004 |
|---|---|---|
| WO | 2004017889 | 3/2004 |

OTHER PUBLICATIONS

Matrx, "Nitronox Field Inhalation Analgesia Machine," Users Manual, date unknown, 13 pages, Orchard Park, New York.

(Continued)

*Primary Examiner* — Steven Douglas
(74) *Attorney, Agent, or Firm* — Trop, Pruner & Hu, P.C.

(57) ABSTRACT

Various embodiments may provide a breathing and/or anesthetic unit that is portable, compact, inexpensive, and convenient, and which may expedite medical procedures by allowing a health care provider to quickly sedate a patient. Such a unit may be ideal for minor medical procedures needing mild or moderate analgesia/sedation (e.g., <30 minutes) in various fields. Such a unit may include (i) a handheld gas supply container including a therapeutic amount of anesthetic gas; (ii) a mask; (iii) a single-use, uninterruptable flow coupler to couple the mask to the supply container; and (iv) a handheld, self-contained, recovery gas container, including a negative pressure, coupled to the mask.

20 Claims, 2 Drawing Sheets

(51) Int. Cl.
*A61M 16/12* (2006.01)
*A61M 16/22* (2006.01)

(52) U.S. Cl.
CPC ............ *A61M 16/12* (2013.01); *A61M 16/205* (2014.02); *A61M 16/22* (2013.01); *A61M 2016/0036* (2013.01); *A61M 2016/0039* (2013.01); *A61M 2016/0042* (2013.01); *A61M 2016/1035* (2013.01); *A61M 2202/0208* (2013.01); *A61M 2202/0241* (2013.01); *A61M 2202/0283* (2013.01); *A61M 2205/3334* (2013.01); *A61M 2230/437* (2013.01); *Y02C 20/10* (2013.01)

(56) References Cited

U.S. PATENT DOCUMENTS

| | | |
|---|---|---|
| 4,265,235 A | 5/1981 | Fukunaga |
| 4,919,132 A | 4/1990 | Miser |
| 5,405,247 A | 4/1995 | Goodman |
| 5,983,891 A | 11/1999 | Fukunaga |
| 5,989,360 A | 11/1999 | Hamilton |
| 6,848,446 B2 | 2/2005 | Noble |
| 6,871,645 B2 | 3/2005 | Wartman |
| 7,178,524 B2 | 2/2007 | Noble |
| 2006/0032509 A1 | 2/2006 | Milles |
| 2006/0111749 A1 | 5/2006 | Westenskow |
| 2008/0110925 A1 | 5/2008 | Hagstrom |
| 2011/0073108 A1 | 3/2011 | Bird |
| 2012/0017908 A1 | 1/2012 | Muellner |

OTHER PUBLICATIONS

Tobias, Joseph D., "Procedural Sedation in Infants and Children: What's New," date unknown, 54 pages, Columbus, Ohio.
Fred Certosimo, "Clinical Evaluation of the Efficacy of Three Nitrous Oxide Scavenging Units During Dental Treatment," American Dental Assistants Association, 2003, pp. 1-9.
Marshall M. Freilich, et al., "Effectiveness of 2 Scavenger Mask Systems for Reducing Exposure to Nitrous Oxide in a Hospital Based Pediatric Dental Clinic: A Pilot Study," JCDA, Sep. 2003, vol. 73, No. 7, pp. 615-615d.

PORTABLE SEDATION APPARATUS AND RELATED METHOD

This application is a continuation of U.S. patent application Ser. No. 13/548,894, filed Jul. 13, 2012, which is a continuation of U.S. patent application Ser. No. 12/569,618, filed Sep. 29, 2009, now U.S. Pat. No. 8,251,058, issued Aug. 28, 2012, the content of which is hereby incorporated by reference.

BACKGROUND

A health care provider (e.g., physician or dentist) may administer nitrous oxide to a patient to alleviate pain or anxiety the patient is experiencing. Because nitrous oxide is minimally metabolized, it retains its potency when exhaled by the patient into the room. The exhaled nitrous oxide can pose an intoxicating and prolonged-exposure hazard to nearby health care providers. Thus, where nitrous oxide is administered, a continuous-flow fresh-air ventilation system or nitrous-scavenging system is used to prevent waste gas buildup.

Typical scavenging systems can be large and external to anesthetic equipment. Such scavenger units may include immobile units that create a negative pressure to remove waste gases exhaled by the patient. The expense and immobility of these systems present obstacles to their use in various environments such as, without limitation, a urology clinic wherein patients may benefit from short periods of anesthetic treatment. In other words, installing conventional, costly, space-intensive, immobile anesthetic units that provide gases (e.g., nitrous oxide) and scavenging capabilities may not be appropriate for meeting the needs of some health care environments such as medical clinics.

BRIEF DESCRIPTION OF THE DRAWINGS

The accompanying drawings, together with the description of embodiments of the invention, explain various embodiments of the invention. In the drawings.

DETAILED DESCRIPTION

The following description refers to the accompanying drawings. Among the various drawings the same reference numbers may be used to identify the same or similar elements. While the following description provides a thorough understanding of the various aspects of the claimed invention by setting forth specific details such as particular structures, architectures, interfaces, and techniques, such details are provided for purposes of explanation and should not be viewed as limiting. Moreover, those of skill in the art will, in light of the present disclosure, appreciate that various aspects of the invention claimed may be practiced in other examples or implementations that depart from these specific details. At certain junctures in the following disclosure, descriptions of known devices and methods have been omitted to avoid clouding the description of the present invention with unnecessary detail.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements co-operate or interact with each other, but they may or may not be in direct physical contact. As used herein, unless otherwise specified, the use of the ordinal adjectives "first", "second", "third", etc., to describe a common object merely indicate that different instances of like objects are being referred to, and are not intended to imply that the objects so described must be in a given sequence, either temporally, spatially, in ranking, or in any other manner. References to "one embodiment", "an embodiment", "example embodiment", "various embodiments", etc., indicate that the embodiment(s) of the invention so described may include particular features, structures, or characteristics, but not every embodiment necessarily includes the particular features, structures, or characteristics. Further, some embodiments may have some, all, or none of the features described for other embodiments.

Figure 1:
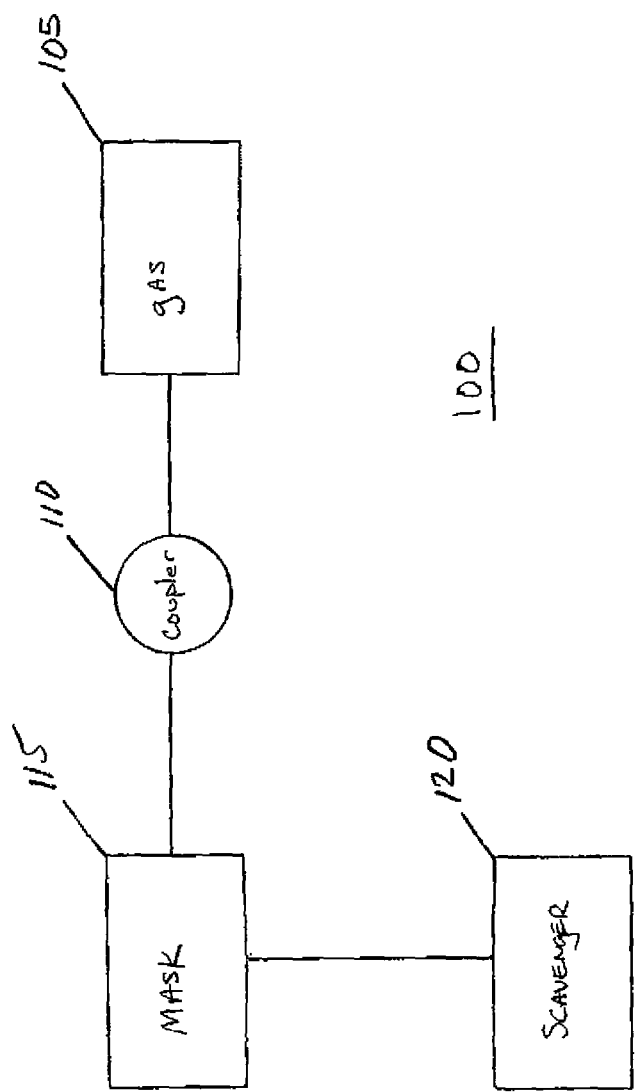
FIGS. 1-3 illustrate block diagrams for various embodiments of the invention.

FIG. 1 illustrates a portable anesthetic and breathing unit 100 in one embodiment of the invention. Block 105 includes a mobile gas container such as a canister pre-filled to emit 30-50% nitrous oxide and, respectively, 70-50% oxygen. The amount of gas, of whatever composition is appropriate for the task at hand, may be sufficient to continuously provide gas for a desired amount of time such as, for example, 30 minutes. Of course other embodiments of the invention may provide longer or shorter periods of gas flow and for gases other than nitrous oxide. Furthermore, in one embodiment of the invention several canisters may be included within block 105. For example, one canister may include nitrous oxide while another canister includes oxygen. The canisters may be packaged together as a single unit.

Block 110 includes a coupler unit to couple the gas container(s) 105 to mask 115. Coupler unit 110 may provide a "one time use" or "single-use" that is "tamper proof" to prevent abuse of gases such as nitrous oxide. In one embodiment of the invention, such a unit may allow gas to continuously flow from the container(s) 105 to mask 115 without the ability for a user to stop the flow of gas (i.e., "uninterruptable"). "Continuous flow" does not necessarily indicate the flow rate is unchanged but that gas flows, as some rate, continuously until the gas supply is exhausted. The uninterruptable gas flow makes it difficult to impossible for a person to save the gas and later use the remaining gas for a purpose not prescribed by the health care provider. If a patient is properly sedated before the gas supply has been fully exhausted, the health care provider may simply increase the gas flow to a rate whereby the supply is quickly exhausted. Such coupling units are known to those of ordinary skill in the art. For example, U.S. Patent Application No. 2008/0110925 (hereinafter '925 Application) includes a control valve for use with portable gas cylinders. Such a control valve, when connected to a portable gas cylinder, may include a setting that ensures the gas in the cylinder is evacuated prior to shipping the cylinder back to a distributor.

In another embodiment of the invention, coupler 110 may include a valve such as the one described in European Patent Application EP 1416218 (hereinafter '218 Application). Such a valve may include a mechanism whereby a ball valve is opened when a rod pierces a membrane and displaces a ball from a socket, thereby allowing gas flow. Modifying the device so that, for example, the rod is barbed and locks in place once it engages the ball may ensure the gas flow would be uninterrupted.

Of course, various embodiments of the invention do not necessarily require such a one-time use valve as described in above.

Block 115 includes a mask for administering gas to a patient. Any number of masks may be used in various embodiments of the invention including, without limitation, non-rebreather mask (NRB), bag valve mask (BVM), pocket mask, etc. A NRB may cover the nose and mouth and couple to a reservoir bag. The NRB may ensure the patient breathes only air from a controlled supply, such as a nitrous oxide canister (or other inhalant).

Block 120 includes a scavenging unit. In one embodiment of the invention the scavenging unit would meet all necessary government regulations (e.g., United States Occupational Safety and Health Administration). The scavenger unit may scavenge (e.g., remove) nitrous oxide (and/or any other waste gas such as carbon dioxide) exhaled by the patient. The scavenger unit may include nitrous oxide absorbing pellets or granules such as those known to persons of ordinary skill in the art. See, e.g., U.S. Pat. Nos. 4,265,235 and 5,983,891. The scavenger unit may also include, as described in U.S. Pat. No. 4,259,303, a catalyst comprising of one or more metal oxides selected from the group consisting of ferric oxide, cobalt oxide, cupric oxide, chromium oxide, manganese dioxide and nickel oxide. When waste gas (e.g., nitrous oxide) contacts the catalyst, which is warmed in a reactor to a temperature of 250 degrees C. to 650 degrees C., the gas may decompose.

Figure 2:
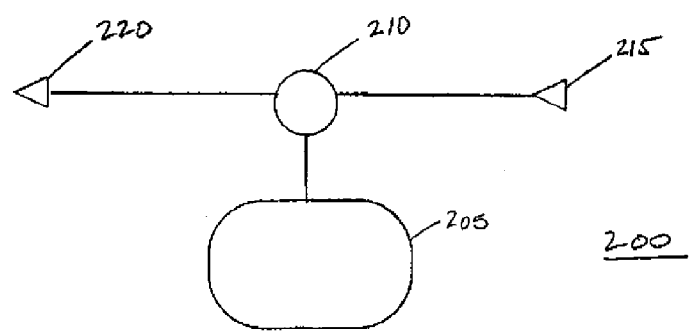

In an embodiment of the invention, the scavenging unit (with or without gas absorbing pellets, catalysts, etc.) may utilize negative pressure to remove waste gases. As detailed more closely in FIG. 2, scavenger unit 200 may also be mobile and may include canister 205. With valve 210 operatively coupling vacuum pump 220 to canister 205, a negative pressure (e.g., less than atmospheric pressure in the patient area or surroundings) may be created in canister 205. "Negative pressure" herein does not necessarily equal less than 0 mmHg. Then, in one embodiment of the invention, pump 220 may then be decoupled from the remainder of the system. Valve 210 may then be adjusted to operatively couple inlet 215 to negatively pressured canister 205. Inlet 215 may couple to mask 115 (FIG. 1). Valve 210 may be adjustable to control the flow rate of exhaled waste gases taken from the patient at inlet 215 and delivered to canister 205. The canister 205 may be sized to maintain sufficient negative pressure, as controlled by adjustable valve 210, for the duration (e.g., 30 minutes) of gas flow from gas canister(s) 105 (FIG. 1).

Figure 3:
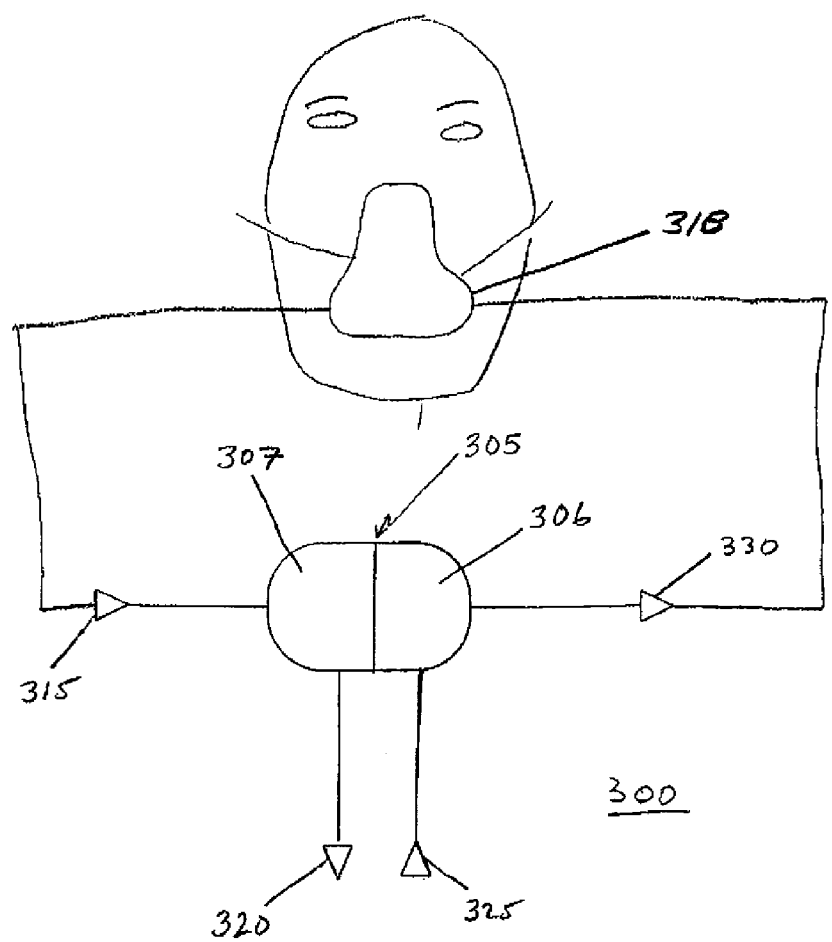

FIG. 3 includes another embodiment of the invention. In system 300, a gas (e.g., nitrous oxide) may be supplied, under pressure, from gas supply 325 to compartment 306 of canister 305. The pressurized gas may flow from compartment 306 to outlet 330, which may couple to coupler 110 (FIG. 1) and/or mask 318. Vacuum pump 320 may create a negative pressure in compartment 307 of canister 305. Inlet 315 may be coupled to negatively pressured compartment 307. Inlet 315 may couple to mask 318. Adjustable valves (not shown) may be used to control outflow of gas at 330 and inflow of gas at 315. Various valves may be used to (e.g., valve 210 of FIG. 2) to simplify the arrangement of system 300. For example, a single coupler may be configured to simultaneously enable nitrous oxide outflow (e.g., from 306) and inflow of waste gas into a scavenging unit (e.g., into 307). This inflow and outflow may be continuous and uninterruptable until the gas supply is exhausted and the exhausted gas is used by the patient or captured by the scavenge unit. The mask, gas supply, and scavenging unit may be coupled together as a unit to resist separating them from one another. This may lessen opportunities for misusing the gas. For example, once nitrous oxide is administered by the health care professional the gas will flow and be used by the patient or captured by the scavenge unit (which may be closely and fixedly coupled to the mask) until exhausted.

The invention is not limited to supplying nitrous oxide for anesthetic purposes. For example, such a unit may be used for other inhalants, including other anesthetic agents wherein a canister including inhalants is used in block 105 of system 100.

Furthermore, various sensors may be included in the invention such as, for example, flow meters to indicate the rate of gas flow and/or sensors to indicate the concentration of nitrous oxide (or any other gas) in the gas stream emitted to and/or taken from the mask.

In one embodiment of the invention, system 100 includes an assortment of various-sized gas canisters. For example, canisters for 5, 10, 15, 20, 25, and 30 minute applications may be supplied or at least made available for use with system 100.

In an embodiment of the invention, the gas canister may be refilled. For example, a spent canister may be refilled in a controlled location of a hospital. As an alternative, the spent canister may be shipped to a distributor for recharging.

The aforementioned embodiments may provide a breathing and/or anesthetic unit that is portable, compact, inexpensive, and convenient, and which may expedite medical procedures by allowing a health care provider to quickly sedate a patient. Such a unit may be ideal for minor medical procedures needing mild or moderate analgesia/sedation (e.g., <30 minutes) in various fields (e.g., cardiovascular, endocrine, otolaryngology, gastrointestinal, hemio/lymphatic, integument, musculoskeletal, nervous, ophthalmology, thoracic, urinary, etc.).

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A mobile sedation system comprising:
    a portable and mobile first gas container including anesthetic gas;
    a second gas container including oxygen;
    a portable and mobile self-contained, scavenging third gas container configured to include a negative pressure, to couple to a mask; and
    a portable and mobile fourth container that fixedly secures the first, second, and third gas containers to one another;
    wherein the mobile system is configured to (i) deliver the oxygen and the anesthetic gas to a patient; and (ii) scavenge waste gas from the patient by recovering, via the negative pressure, the waste gas into the third gas container.

2. The system of claim 1, wherein the third gas container is configured to couple to a vacuum source to charge the third gas container with the negative pressure.

3. The system of claim 1 including a set of anesthetic gas containers, the set including the first gas container and additional gas containers; wherein each of the first and additional gas containers include different amounts of gases.

4. The system of claim 1, wherein the first gas container includes at least a 15 minute supply of the anesthetic gas.

5. The system of claim 4, wherein the third gas container includes at least a 15 minute supply of the negative pressure.

6. The system of claim 1 including a single-use, uninterruptable flow coupler to couple the mask to the first container.

7. The system of claim 6, wherein the coupler is configured to simultaneously enable initial gas flow out of the first gas container and initial gas flow into the third gas container.

8. A portable and mobile sedation system comprising:
    a portable and mobile first gas container including anesthetic gas;
    a second gas container including oxygen; and a portable and mobile, self-contained, scavenging third gas container, to couple to a mask;

wherein the portable and mobile system is configured to (i) deliver the oxygen and the anesthetic gas to a patient; and (ii) scavenge waste gas from the patient by recovering, via negative pressure, the waste gas into the third gas container;

wherein the third gas container is configured to couple to a vacuum source to charge the third gas container with the negative pressure.

9. The system of claim 8 including a portable and mobile fourth container configured to couple to and secure the first, second, and third gas containers to each other.

10. The system of claim 8 including a set of anesthetic gas containers, the set including the first gas container and additional gas containers; wherein each of the first and additional gas containers include different amounts of gases.

11. The system of claim 8 including a portable and mobile separate unit configured to secure the first, second, and third gas containers to each other.

12. The system of claim 8, wherein the first gas container includes at least a 15 minute supply of the anesthetic gas.

13. The system of claim 12, wherein the third gas container includes at least a 15 minute supply of the negative pressure.

14. The system of claim 8 including a single-use, uninterruptable flow coupler to couple the mask to the first gas container.

15. A mobile sedation system comprising:
a mobile first gas container including anesthetic gas;
a second gas container including oxygen;
a mobile, self-contained, scavenging third gas container to couple to a mask;
wherein the mobile system is configured to (i) deliver the oxygen and the anesthetic gas to a patient; and (ii) scavenge waste gas from the patient by recovering, via negative pressure, the waste gas into the third gas container;
wherein the third gas container is configured to couple to a vacuum source to charge the third gas container with the negative pressure.

16. The system of claim 15 comprising a single-use, uninterruptable flow coupler to couple the mask to the first container, wherein the coupler is configured to enable initial gas flow out of the first gas container and initial gas flow into the third gas container each in an uninterruptable and continuous manner.

17. The system of claim 15 including-a mobile separate unit configured to secure the first, second, and third gas containers to each other.

18. The system of claim 2 comprising the vacuum source, wherein the vacuum source includes a vacuum pump.

19. The system of claim 8 comprising the vacuum source, wherein the vacuum source includes a vacuum pump.

20. The system of claim 15 comprising the vacuum source, wherein the vacuum source includes a vacuum pump.

* * * * *